(12) United States Patent
Rivers et al.

(10) Patent No.: US 7,314,951 B2
(45) Date of Patent: Jan. 1, 2008

(54) PROCESS AND COMPOSITION FOR LOWER TOXICITY QUATERNARY AMMONIUM COMPOUNDS

(75) Inventors: Gordon T. Rivers, Houston, TX (US); Joann McMahon, Arnold, MO (US)

(73) Assignee: Baker Hughes Incorporated, Houston, TX (US)

( * ) Notice: Subject to any disclaimer, the term of this patent is extended or adjusted under 35 U.S.C. 154(b) by 393 days.

(21) Appl. No.: 10/945,121

(22) Filed: Sep. 20, 2004

(65) Prior Publication Data

US 2005/0069515 A1  Mar. 31, 2005

Related U.S. Application Data

(60) Provisional application No. 60/506,044, filed on Sep. 25, 2003.

(51) Int. Cl.
*C07C 229/00* (2006.01)
(52) U.S. Cl. .................................................... 560/155
(58) Field of Classification Search ...................... None
See application file for complete search history.

(56) References Cited

U.S. PATENT DOCUMENTS

| | | | | |
|---|---|---|---|---|
| 2,367,878 A | * | 1/1945 | Lee | 560/38 |
| 2,785,978 A | * | 3/1957 | de Rijck | 99/23 |
| 4,020,155 A | | 4/1977 | Kalopissis et al. | |
| 4,038,459 A | | 7/1977 | Ajami et al. | |
| 4,113,591 A | | 9/1978 | Laundon et al. | |
| 4,124,632 A | | 11/1978 | Kalopissis et al. | |
| 4,585,835 A | | 4/1986 | Saegusa et al. | |
| 4,790,978 A | | 12/1988 | Allenmark et al. | |
| 4,943,612 A | | 7/1990 | Morita et al. | |
| 5,080,902 A | | 1/1992 | Allenmark et al. | |
| 5,144,060 A | | 9/1992 | Morita et al. | |
| 5,204,060 A | | 4/1993 | Allenmark et al. | |
| 5,354,906 A | * | 10/1994 | Weitemeyer et al. | 554/52 |
| 5,429,755 A | | 7/1995 | Ilardi et al. | |
| 5,527,477 A | | 6/1996 | Ilardi et al. | |
| 5,607,691 A | | 3/1997 | Hale et al. | |
| 5,663,138 A | | 9/1997 | Ilardi et al. | |
| 5,798,095 A | | 8/1998 | Racky | |
| 5,858,960 A | | 1/1999 | Conroy et al. | |
| 5,925,444 A | | 7/1999 | Katsumura et al. | |
| 5,958,870 A | | 9/1999 | Declercq et al. | |
| 5,961,999 A | | 10/1999 | Bimczok et al. | |
| 6,048,835 A | * | 4/2000 | Durbut et al. | 510/426 |
| 6,096,701 A | | 8/2000 | Mondin et al. | |
| 6,184,197 B1 | | 2/2001 | Heinzman et al. | |
| 6,315,991 B1 | * | 11/2001 | Zofchak et al. | 424/70.28 |
| 6,346,259 B1 | | 2/2002 | Terasaki et al. | |
| 6,384,266 B1 | | 5/2002 | Farone et al. | |
| 6,486,333 B1 | | 11/2002 | Murayama et al. | |
| 6,586,639 B2 | | 7/2003 | Murayama et al. | |
| 6,620,330 B2 | | 9/2003 | Rivers et al. | |
| 6,723,249 B2 | | 4/2004 | Rivers et al. | |

FOREIGN PATENT DOCUMENTS

| | | |
|---|---|---|
| DE | 3618517 A1 | 12/1986 |
| EP | 0 752 465 A1 | 1/1997 |
| EP | 1 016 650 A1 | 12/1999 |

OTHER PUBLICATIONS

A. Sismondi, et al., "Synthesis de Nouveaux Intermediaires F-alkyles Precurseurs de Tensioactifs Cationiques Hautement Fluores", Journal of Fluorine Chemistry, 1992, pp. 127-132, vol. 59.
Database Beilstein Abstract, Beilstein Institute for Organic Chemistry, Frankfurt-Main, DE, 1994, XP002319981, Database accession No. 6886739.
PCT International Search Report for PCT/US2004/031262, Mar. 17, 2005.

* cited by examiner

Primary Examiner—Sikarl A. Witherspoon
(74) Attorney, Agent, or Firm—Madan Mossman & Sriram PC

(57) ABSTRACT

Betaine ester quaternary ammonium compounds with reduced toxicity and improved biodegradability are formed by esterification of a haloacetic acid with an alcohol containing at least 4 carbon atoms, followed by quaternization of the halo-acetate with a tertiary amine containing at least 4 carbon atoms. In one non-limiting embodiment the alkyl substituents on the nitrogen of the tertiary amine have at least 2 carbon atoms, and in another non-limiting embodiment are each n-butyl.

11 Claims, 1 Drawing Sheet

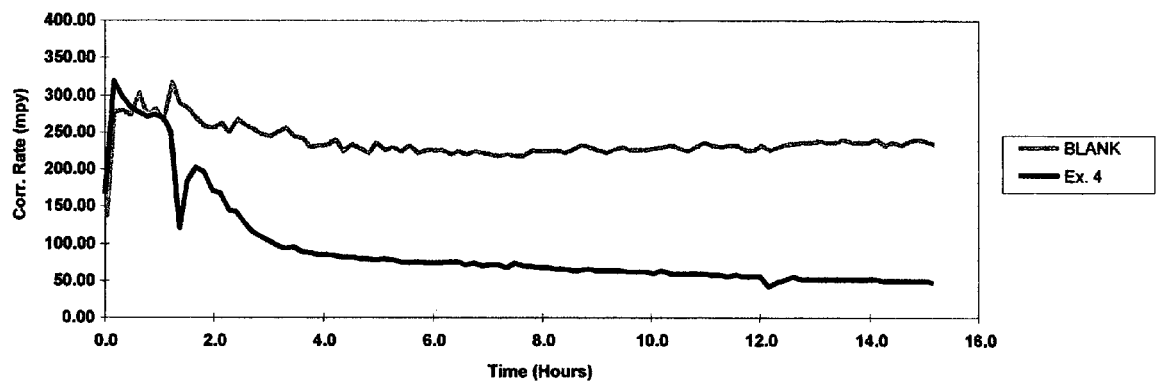

PROCESS AND COMPOSITION FOR LOWER TOXICITY QUATERNARY AMMONIUM COMPOUNDS

CROSS-REFERENCE TO RELATED APPLICATION

This application claims the benefit of U.S. provisional application No. 60/506,044 filed Sep. 25, 2003.

FIELD OF THE INVENTION

The invention relates to quaternary ammonium compounds having reduced toxicity and improved biodegradability and methods for producing these compounds, and, in one aspect more particularly relates to betaine ester quaternary ammonium compounds and methods for making them.

BACKGROUND OF THE INVENTION

It is well known that quaternary onium compounds, particularly quaternary ammonium compounds such as quaternary ammonium salts, have found widespread use in a number of applications including, but not necessarily limited to, disinfectants, cleanser and sterilizers, cosmetics (deodorants, dandruff removers, emulsion stabilizers), fungicides, mildew preventatives, antistatic additives, biocides, to increase the affinity of dyes for photographic film, to improve dispersibility in the coatings of pigment particles, to increase adhesion of road dressings and paints, and in applications related to oil and gas production and transportation including, but not necessarily limited to, surfactants, dispersants, biocides, corrosion inhibitors, etc. Because quaternary onium compounds function as biocides whether or not this is their originally intended purpose, the residual quaternary onium compounds when discharged into waste water streams after use will interfere in the biological treatment processes by inhibiting the growth of biomass. Additionally, in situations such as discharging used water directly into the environment, such as into seawater, the discharge of water containing quaternary onium compounds may be restricted due to regulations pertaining to the toxicity of such water to marine organisms.

U.S. Pat. No. 4,204,954 concerns the detoxification of residues of quaternary ammonium salt biocides in water using neutralizing amounts of anionic monomers.

There remains a need for new compositions that perform the necessary tasks, but that have improved biodegradability over previously evaluated quaternary compounds and reduced toxicity concerns and so that they can be safely discharged and/or be readily treated using conventional wastewater treatment with biomass.

SUMMARY OF THE INVENTION

Accordingly, it is an object of the present invention to provide quaternary ammonium compounds that have reduced toxicity concerns.

It is another object of the present invention to provide a method for reducing the toxicity of quaternary ammonium compounds that can be readily implemented.

It is yet another object of the invention to provide betaine ester quaternary ammonium compounds and methods for producing them.

In carrying out these and other objects of the invention, there is provided, in one form, betaine ester quaternary ammonium compounds formed by esterifying a haloacetic acid with an alcohol having at least 4 carbon atoms to give a haloacetate. The haloacetate is then quaternized with a tertiary amine having at least 4 carbon atoms.

In another non-limiting embodiment of the invention there are provided betaine ester quaternary ammonium compound having the formula:

(I)

where R are each independently straight, branched, saturated or unsaturated hydrocarbon groups having at least two carbon atoms, where R1 is an alcohol residue having at least four carbon atoms, and where A is selected from the group consisting of hydroxide anion, halide anions, carboxylate anions, sulfate anion, organic sulfonate anions, and mixtures thereof.

In another non-limiting embodiment of the invention there is provided a method of making betaine ester quaternary ammonium compounds that involves esterifying a haloacetic acid with an alcohol having at least 4 carbon atoms to give a haloacetate, and quaternizing the haloacetate with a tertiary amine having at least 4 carbon atoms.

BRIEF DESCRIPTION OF THE DRAWING

The FIGURE is a chart of the results of corrosion testing for an oil soluble inhibitor of Example 4 in a 90% NACE brine with 10% Isopar M at a concentration of 10,000 ppm at 140° F. (60° C.) over a period of about 15 hours.

DETAILED DESCRIPTION OF THE INVENTION

These novel betaine ester quaternary ammonium compounds are part of the class historically known as betaine esters. Betaine is $(CH_3)_3N^{3O}CH_2COO^-$. According to the Merck Index (betaine, entry number 1201, 11th edition), betaine is widely distributed in plants and animals. Betaine is ubiquitous and essentially nontoxic. In water, betaine esters eventually hydrolyze to betaine and an alcohol.

In this invention, betaine type esters are made and discovered to have relatively low toxicity concerns compared to conventional quaternary ammonium compounds. The three methyl groups of betaine are replaced by larger alkyl groups. In one non-limiting embodiment of the invention, the methyl groups are replaced by ethyl groups. In an alternate non-limiting embodiment, the methyl groups are replaced by n-propyl groups. In another non-limiting embodiment of the invention, the methyl groups are replaced by n-butyl groups. It is not necessary that the methyl groups are replaced by the same unsaturated or saturated hydrocarbon group, although they may be and typically are. In another non-limiting embodiment of the invention the methyl groups are replaced by hydrocarbon groups including, but not necessarily limited to, n-propyl, n-butyl, i-butyl, allyl, 2-butenyl, 3-butenyl, methallyl, n-pentyl, i-pentyl, 2-pentenyl, 3-pentenyl, and 4-pentenyl, and combinations thereof.

The alcohol residue in the betaine type ester has at least 4 carbon atoms in one non-limiting embodiment of the invention, and at least 7 carbon atoms in an alternate non-limiting embodiment. In still another non-limiting embodiment of the invention, the alcohol has at least 10 carbon atoms. A maximum number of carbon atoms is not known, but may be about 40 in one non-limiting embodiment of the invention. The alcohol group, residue or moiety may also contain hetero atoms such as oxygen, nitrogen, sulfur, phosphorus or silicon.

The alcohol may be a commercially available alcohol. These include, but are not necessarily limited to, linear alcohols such as those sold by Sasol under the trade name Alfol, ethoxylated linear alcohols such as those sold by Sasol under the trade name Alfonic, Guerbet type alcohols such as those sold by Sasol under the trade name Isofol, branched alcohols such as those sold by Exxon Mobil under the trade name Exxal, and ethoxylated phenols such as those sold by Huntsman under the trade name Surfonic. Alcohols that have been alkoxylated with alkylene oxides other than ethylene oxide, such as propylene oxide and butylenes oxide, either randomly or in blocks, are also within the definition of suitable alcohols in this invention.

The alcohol may also be prepared by the ring opening of an epoxide with approximately one mole equivalent of a compound containing one hydroxyl group. Compounds containing one hydroxyl group include the alcohols described above and carboxylic acids containing 1 to 30 carbon atoms.

The alcohol may also be prepared by transesterification of vegetable oil or animal oil with a second substance containing at least two hydroxyl groups. Vegetable oils include, but are not necessarily limited to, corn oil, coconut oil, soybean oil, cotton seed oil, flax seed oil and the like. Suitable animal oils include, but are not necessary limited to, tallow, acylglycerol, blubber, cod liver oil, fish oil, glyceride, goose grease, lanolin, lard oil, sperm oil, wool oil, and the like. Suitable substances containing at least two hydroxyl groups include but are not necessarily limited to, ethylene glycol, propylene glycol, glycerin, trimethylolpropane, neopentyl glycol and sorbitol. All of these compounds are encompassed in the definition of alcohol for this invention.

Suitable haloacetic acids include, but are not necessarily limited to, fluoroacetic acid, chloroacetic acid, bromoacetic acid, iodoacetic acid, and mixtures thereof. The esterification of the haloacetic acid with the alcohol may occur at atmospheric pressure and a temperature in the range of about 60 to about 250° C., in one non-limiting embodiment of the invention. In another non-limiting embodiment, the esterification temperature is in the range of about 80 to about 180° C. The molar ratio of haloacetic acid to alcohol in the esterification reaction may range from about 0.2 to about 2.0, preferably from about 0.5 to about 1.2.

The esterification may be acid catalyzed using small, catalytic amounts of mineral acid or organic acid catalysts. Specific, non-limiting examples of suitable inorganic acid catalysts for the method herein include sulfuric acid, sulfamic acid, phosphorous acid, phosphoric acid, and the like, while suitable organic acids include p-toluenesulfonic acid monohydrate, methanesulfonic acid, dodecyl-benzene-sulfonic acid (DDBSA), and the like. Suitable organometallic (non-acidic) catalysts for the esterification include, but are not necessarily limited to, dibutyltin oxide, dibutyltin laurate, titanium tetra(isopropoxide), and the like. In another non-limiting embodiment of the invention, the reaction mixture is contacted with nitrogen until the acid number of the mixture is below about 3 before the quaternization.

The esterification of the haloacetic acid gives a haloacetate, which in turn is quaternized according to any of the known processes or methods using a tertiary amine. In one non-limiting embodiment, the quaternization is conducted at a temperature in the range of about 10 to about 120° C. In another non-limiting embodiment of the invention, the quaternization temperature is in the range of about 25 to about 100° C. In an alternate, non-restrictive embodiment of the invention, the quaternization is conducted in the absence of an alcohol. In another non-limiting embodiment, the mole ratio of haloacetate to tertiary amine in the quaternization is about 1:1.

The tertiary amine used in the quaternization should have at least four carbon atoms. In another non-limiting embodiment of the invention, the tertiary amine has the formula $NR_3$, and each R group has at least two carbon atoms. In one non-limiting embodiment of the invention, R are independently hydrocarbon groups including, but not necessarily limited to, ethyl, n-propyl, n-butyl, i-butyl, allyl, 2-butenyl, 3-butenyl, methallyl, n-pentyl, i-pentyl, 2-pentenyl, 3-pentenyl, and 4-pentenyl, and combinations thereof. In a particular non-limiting embodiment of the invention, each R group is an n-butyl group. Each of the R groups on the tertiary amine need not be identical, although they may be.

The betaine ester quaternary ammonium compounds of this invention may have the formula:

(I)

where R are each independently straight, branched, saturated or unsaturated hydrocarbon groups having at least two carbon atoms, where R1 is an alcohol residue having at least four carbon atoms, and where A is selected from the group consisting of hydroxide anion, halide anions, carboxylate anions, sulfate anion, organic sulfonate anions, and mixtures thereof. The R groups may also be defined as above with respect to the tertiary amines. In one non-limiting embodiment of the invention, the anion A is hydroxide anion.

As will be demonstrated, the betaine ester quaternary ammonium compounds of this invention have reduced toxicity concerns compared to conventional quaternary ammonium compounds. The betaine ester quaternary ammonium compounds are expected to be useful in a number of applications including, but not necessarily limited to, disinfectants, cleanser and sterilizers, cosmetics (deodorants, dandruff removers, emulsion stabilizers), fungicides, mildew preventatives, antistatic additives, biocides, to increase the affinity of dyes for photographic film, to improve dispersibility in the coatings of pigment particles, to increase adhesion of road dressings and paints, and in applications related to oil and gas production and transportation including, but not necessarily limited to surfactants, dispersants, biocides, corrosion inhibitors, etc.

The invention will be further illustrated with reference to actual examples that are not intended to limit the invention, but rather to more completely describe it.

EXAMPLE 1

A solution of 122.91 gm of Alfol 1214, 0.54 gm of p-toluenesulfonic acid monohydrate, 26.13 gm of bromoacetic acid, and 33.55 gm of chloroacetic acid was heated at 140° C. with stirring and sparged with a stream of nitrogen until the acid number of the mixture was below 3. The solution was then cooled to 65° C. and 114.84 gm of tributylamine is added. The solution was kept at 65° C. for 24 hours to give the end product as a clear amber liquid.

EXAMPLE 2

A mixture of 17.49 gm of trimethylolpropane, 171.06 gm of coconut oil, and 0.18 gm of methanesulfonic acid was heated with stirring under nitrogen for 3 hours at 140° C. to give a bright clear solution. To this solution were added 16.47 gm of bromoacetic acid and 22.41 gm of chloroacetic acid. The solution was stirred, sparged with nitrogen and heated at 140° C. until the acid number was below 3. The solution was cooled to 65° C. and 72.39 gm of tributylamine was added. The solution was kept at 65° C. for 24 hours to give the end product as a clear amber liquid.

EXAMPLE 3

Comparative toxicity analysis was conducted for the quaternary ammonium compound from Example 2 and for benzyldimethylcoco ammonium chloride, a commercial quaternary ammonium compound. Results from range-finding toxicity studies indicate that the Example 2 compound is less toxic to marine species as compared to benzyldimethylcoco ammonium chloride.

EXAMPLE 4

The material of Example 2 was incorporated into the oil soluble inhibitor composition of Table I and tested for corrosion inhibition.

TABLE I

Oil Soluble Inhibitor Composition

| Component | Wt % |
|---|---|
| Example 2 material | 39.1 |
| Methanesulfonic acid | 0.9 |
| Aromatic solvent | 58.0 |
| NEODOL 45-12 | 0.4 |
| NEODOL 45-7 | 0.26 |
| Mixed alkyl pyridines | 1.34 |

NEODOL 45-12 and NEODOL 45-7 are both ethoxylated alcohols available from Shell Chemical Company. The Example 4 composition was tested at a concentration of 10,000 ppm at 140° F. (60° C.) in a 90% NACE brine with 10% Isopar M using a steel coupon in an electrochemical test, and compared against a blank run. The blank corrosion rate was 234 mpy, whereas the inhibited rate was 48.2 yielding a 79.4% protection factor. These results are charted in the FIGURE.

Many modifications may be made in the present invention without departing from the spirit and scope thereof that are defined only by the appended claims. For example, certain reactants, such as haloacetic acids, alcohols, or tertiary amines other than those specifically set out herein or other acid catalysts may be found by one of routine skill in the art to be particularly advantageous. Further, it may be found that certain betaine ester quaternary ammonium compounds give especially good results in a particular application or have especially reduced toxicity concerns or improved biodegradability over other quaternary compounds previously evaluated.

We claim:

1. Betaine ester quaternary ammonium compounds formed by the process comprising
   esterifying a haloacetic acid selected from the group consisting of fluoroacetic acid, chloroacetic acid, bromoacetic acid, iodoacetic acid, and mixtures thereof, with an alcohol having at least 4 carbon atoms to give a haloacetate, where the alcohol is selected from the group consisting of alcohols obtained by the transesterification of an animal or vegetable oil with a compound having at least two hydroxyl groups, where the alcohol may be substituted with one or more heteroatoms selected from the group consisting of oxygen, nitrogen, sulfur, phosphorus, and silicon; and
   quaternizing the haloacetate with a tertiary amine having the formula $NR_3$, wherein each R group independently is selected from the group consisting of n-propyl, n-butyl, i-butyl, allyl, 2-butenyl, 3-butenyl, methallyl, n-pentyl, i-pentyl, 2-pentenyl, 3-pentenyl, and 4-pentenyl, in the absence of an alcohol.

2. The betaine ester quaternary ammonium compounds of claim 1 where the tertiary amine has at least 9 carbon atoms.

3. A betaine ester quaternary ammonium compound having the formula:

$$R1-OC(=O)-CH_2-N^+R_3 \; A^- \qquad (I)$$

where R are each independently selected from the group consisting of n-propyl, n-butyl, i-butyl, allyl, 2-butenyl, 3-butenyl, methallyl, n-pentyl, i-pentyl, 2-pentenyl, 3-pentenyl, and 4-pentenyl, where R1 is an alcohol residue having at least four carbon atoms selected from the group consisting of alcohols obtained by the transesterification of an animal or vegetable oil with a compound having at least two hydroxyl groups, where the alcohol may be substituted with one or more heteroatoms selected from the group consisting of oxygen, nitrogen, sulfur, phosphorus, and silicon, and where A is selected from the group consisting of hydroxide anion, halide anions, carboxylate anions, sulfate anion, organic sulfonate anions, and mixtures thereof.

4. The betaine ester of claim 3 where A is selected from the group consisting of hydroxide anion, chloride anion, bromide anion, iodide anion, and mixtures thereof.

5. A method of making betaine ester quaternary ammonium compounds comprising:
   esterifying a haloacetic acid with an alcohol having at least 4 carbon atoms, where the alcohol is obtained by the transesterification of an animal or vegetable oil with a compound having at least two hydroxyl groups, where the alcohol may be substituted with one or more heteroatoms selected from the group consisting of oxygen, nitrogen, sulfur, phosrhorus, and silicon, to give a haloacetate, and
   quaternizing the haloacetate with a tertiary amine having the formula $NR_3$, and each R group has at least two carbon atoms, in the absence of an alcohol.

6. The method of claim 5 where the haloacetic acid is selected from the group consisting of fluoroacetic acid, chloroacetic acid, bromoacetic acid, iodoacetic acid, and mixtures thereof.

7. The method of claim 5 where the tertiary amine has at least 9 carbon atoms.

8. The method of claim 5 where the R groups in the tertiary amine are independently hydrocarbon groups selected from the group consisting of n-propyl, n-butyl, i-butyl, allyl, 2-butenyl, 3-butenyl, methallyl, n-pentyl, i-pentyl, 2-pentenyl, 3-pentenyl, and 4-pentenyl.

9. The method of claim 5 where
the esterifying is conducted at a temperature between about 60 and about 250° C.; and
the quaternizing is conducted at a temperature between about 10 and about 120° C.

10. A method of making betaine ester quaternary ammonium compounds comprising:
esterifying a haloacetic acid selected from the group consisting of fluoroacetic acid, chloroacetic acid, bromoacetic acid, iodoacetic acid, and mixtures thereof with an alcohol having at least 4 carbon atoms, where the alcohol is obtained by the transesterification of an animal or vegetable oil with a comround having at least two hydroxyl groups, where the alcohol may be substituted with one or more heteroatoms selected from the group consisting of oxygen, nitrogen, sulfur, rhosrhorus, and silicon, at a temperature between about 60 and about 250° C. to give a haloacetate, and
quaternizing the haloacetate with a tertiary amine having the formula $NR_3$, and each R group has at least two carbon atoms, at a temperature between about 10 and about 120° C., in the absence of an alcohol.

11. The method of claim 10 where the tertiary amine has at least 9 carbon atoms.

* * * * *